US009326881B1

(12) United States Patent
Press

(10) Patent No.: US 9,326,881 B1
(45) Date of Patent: May 3, 2016

(54) MULTI-LAYER TORSO WRAP FOR BACK PAIN RELIEF HAVING ELASTICITY AND WATER-RETAINING CAPACITY

(71) Applicant: Roberta Press, Del Ray Beach, FL (US)

(72) Inventor: Roberta Press, Del Ray Beach, FL (US)

( * ) Notice: Subject to any disclaimer, the term of this patent is extended or adjusted under 35 U.S.C. 154(b) by 0 days.

(21) Appl. No.: 14/628,739

(22) Filed: Feb. 23, 2015

(51) Int. Cl.
*A61F 5/02* (2006.01)

(52) U.S. Cl.
CPC ........................................ *A61F 5/02* (2013.01)

(58) Field of Classification Search
CPC .................. A61F 2007/001; A61F 2007/0024; A61F 2007/0027; A61F 5/02; A61F 5/028; A61F 2007/0018; A61F 2007/0022–2007/0026; A61F 5/022; A61F 5/024; A61F 5/026; A61F 5/03
USPC ............................................................ 2/467
See application file for complete search history.

(56) References Cited

U.S. PATENT DOCUMENTS

| | | | |
|---|---|---|---|
| 1,491,539 A | 4/1924 | Kirschmann | |
| 3,815,610 A | 6/1974 | Winther | |
| 3,888,248 A | 6/1975 | Moore et al. | |
| 3,889,684 A * | 6/1975 | Lebold | 607/109 |
| 4,106,477 A | 8/1978 | Feld | |
| 4,204,543 A | 5/1980 | Henderson | |
| 4,366,804 A | 1/1983 | Abe | |
| 4,475,543 A * | 10/1984 | Brooks et al. | 602/19 |
| 4,556,055 A * | 12/1985 | Bonner, Jr. | 604/304 |
| 4,688,572 A | 8/1987 | Hubbard et al. | |
| 4,909,244 A | 3/1990 | Quarfoot et al. | |
| 5,133,348 A | 7/1992 | Mayn | |
| 5,409,500 A | 4/1995 | Dyrek | |
| 5,728,147 A | 3/1998 | Thomas | |
| 5,741,318 A | 4/1998 | Ouellette et al. | |
| 5,860,945 A | 1/1999 | Cramer et al. | |
| 6,251,131 B1 | 6/2001 | Kohout | |
| 6,309,369 B1 * | 10/2001 | Lebovic | 602/75 |
| 6,348,212 B2 | 2/2002 | Hymes et al. | |
| 7,591,810 B2 | 9/2009 | Morman et al. | |
| 7,745,687 B2 | 6/2010 | Heyn et al. | |
| 8,079,992 B2 | 12/2011 | Bissan et al. | |

(Continued)

FOREIGN PATENT DOCUMENTS

| | | |
|---|---|---|
| EP | 0965314 | 12/1999 |
| WO | 2007036004 | 4/2007 |

OTHER PUBLICATIONS

Kendall/Covidien, Kendall Tenderso Wet-Pruf Abdominal Pad,8"×10" Sterile,18/Pack, https://www.google.com/shopping/product/13792252284781622410?q=threelayer+moistpack&biw=1236&bih=585&ei=hNsVVMHIHvLCsASfhlHwCg&ved=0CIYBEKYrMAE, Sep. 10, 2014.

Spenco Medical Corporation, 2nd Skin®, http://www.ebay.com/itm/2nd-Skin-1-5-034-x-2-034-3-pack-30-1099-/181460714936?_trksid=p2054897.I4275, Sep. 10, 2014.

(Continued)

*Primary Examiner* — Kari Petrik
(74) *Attorney, Agent, or Firm* — Michael J. Colitz, Jr.

(57) ABSTRACT

A torso wrap is disclosed for providing relief to a person suffering from back pain, including: an inner layer of water-retaining material; a middle layer of moisture-barrier material; and an outer layer of stretchable material having first and second securing ends that secure to each other when the torso wrap is placed around the torso of a person. The inner layer is configured to be moistened with water and is worn in contact with the torso of a person wearing the torso wrap. The middle moisture-barrier layer is attached to the inner layer so as to trap moisture within the inner layer. The middle layer is attached to the outer layer of stretchable material that includes attachment ends for securing the torso wrap around the torso of a person.

1 Claim, 3 Drawing Sheets

(56) References Cited

U.S. PATENT DOCUMENTS

| | | | |
|---|---|---|---|
| 8,314,283 B2 | 11/2012 | Kingsford et al. | |
| 2012/0283615 A1 | 11/2012 | Malik et al. | |
| 2013/0066409 A1* | 3/2013 | Hilton | 607/110 |
| 2014/0005617 A1 | 1/2014 | Choi et al. | |

OTHER PUBLICATIONS

Archives of Trauma Research Center Kashan University of Medical Sciences, OpSite sheets, http://archtraurna.com/?page=articte&article_id=5392, Sep. 10, 2014.

* cited by examiner

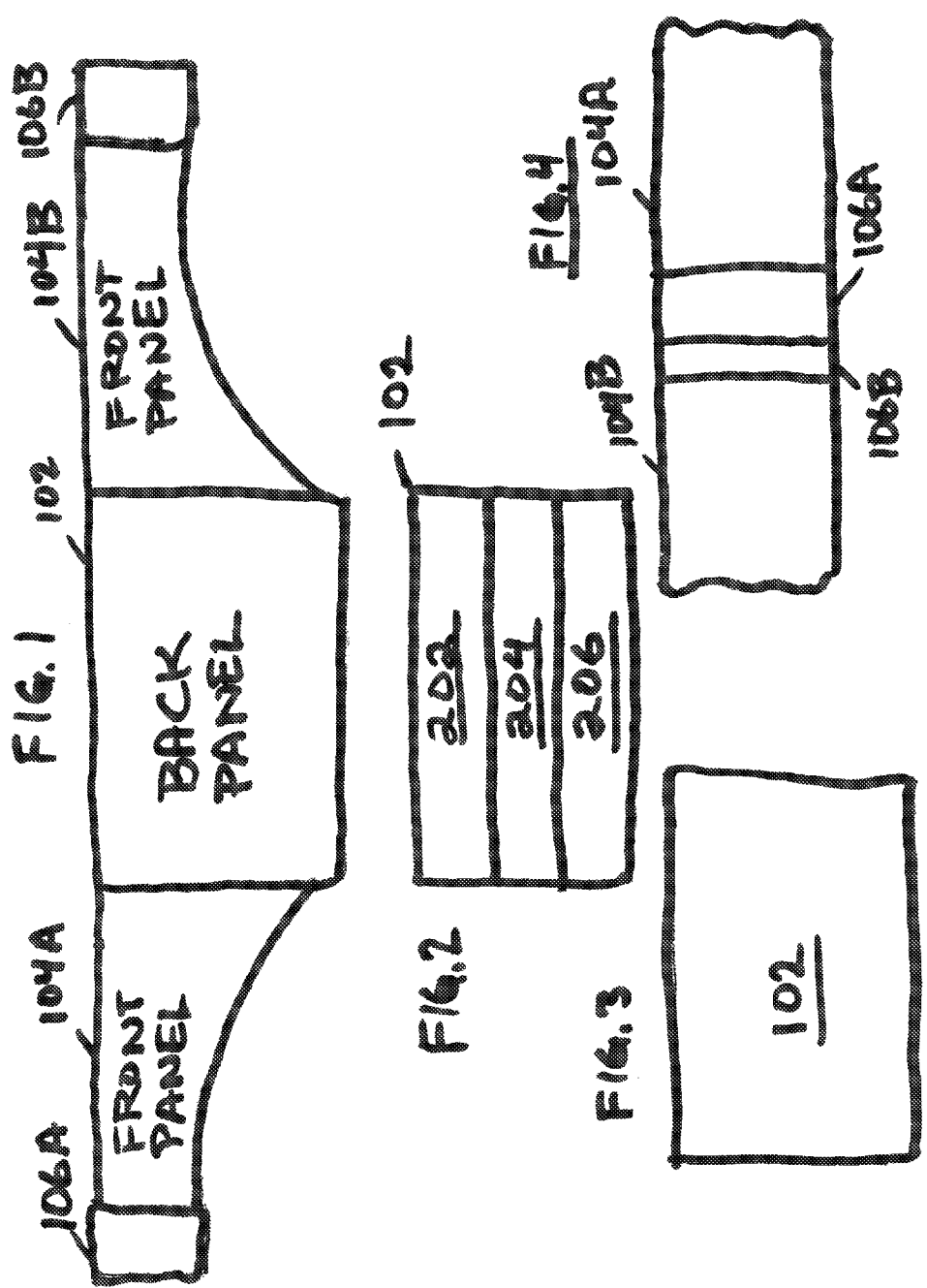

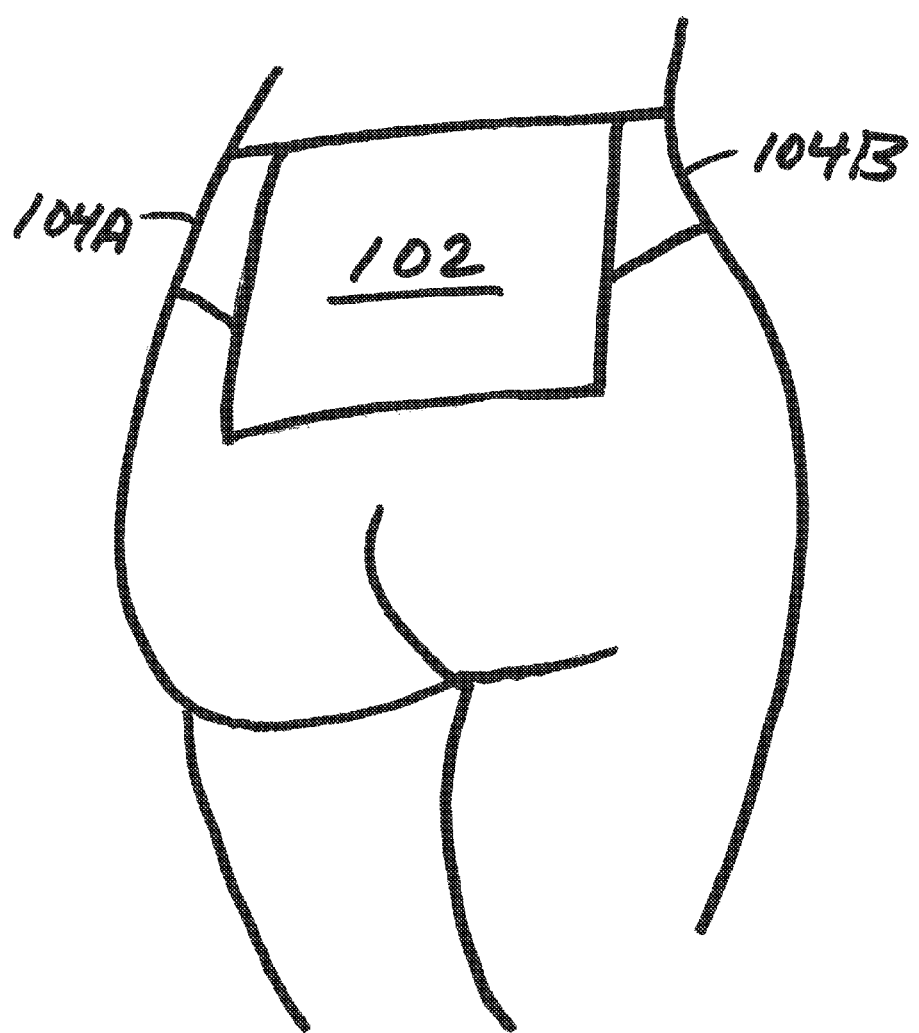

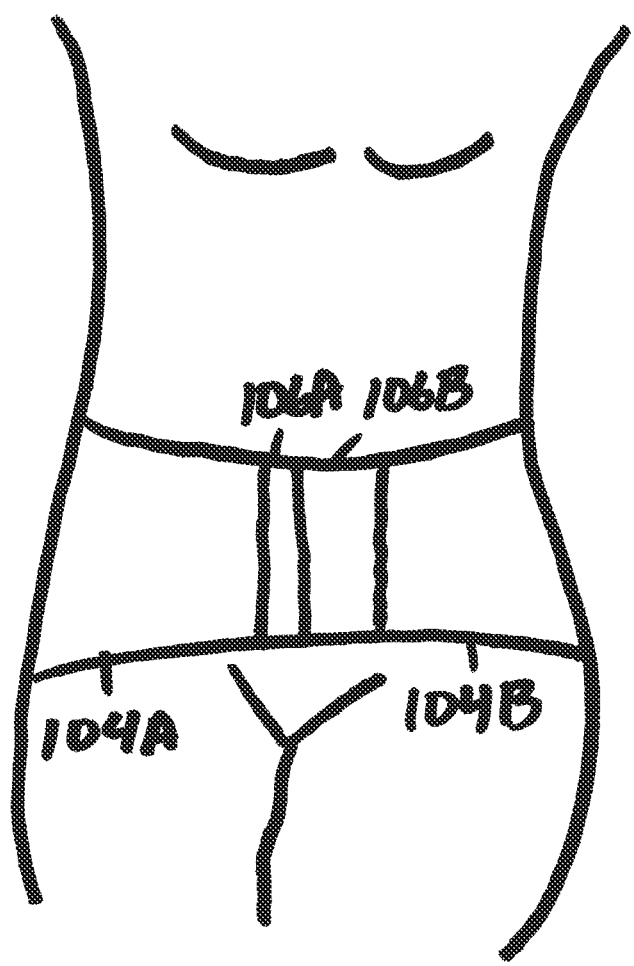

US 9,326,881 B1

MULTI-LAYER TORSO WRAP FOR BACK PAIN RELIEF HAVING ELASTICITY AND WATER-RETAINING CAPACITY

FIELD OF THE INVENTION

The present invention relates generally to wraps and bandages, and more particularly to wraps worn for pain relief.

BACKGROUND OF THE INVENTION

Pain is part of the human condition. In our daily lives, routine activities in which we engage are often sources of muscle strain, dislocation of the spine, and other manifestations of the human body not being able to keep up with the demands that we all place on ourselves. While various around-the-body wraps exist in a wide variety of configurations, the effectiveness of such body wraps applied to a wearer's torso for pain relief remains an area in which improvements are needed.

SUMMARY OF THE INVENTION

The present invention provides a wearable, three-layer torso wrap that is worn by a person seeking back pain relief in a secure manner for a period of time. In one general aspect, the present invention provides a torso wrap for providing relief to a person suffering from back pain, including: an inner layer of water-retaining material; a middle layer of moisture-barrier material; and an outer layer of stretchable material having first and second securing ends that secure to each other when the torso wrap is placed around the torso of a person.

The inner layer of water-retaining material is configured to be moistened with water and worn in contact with the torso of a person wearing the torso wrap. The inner surface of middle moisture-barrier layer can be made from a moisture-resistant plastic, rubber, or silicone material, and is attached to the inner layer to trap moisture therein. The outer surface of the middle moisture-barrier layer is attached to the outer layer of stretchable material. In some embodiments, the first and second ends of the outer layer include a hook-and-loop fastener system. In some embodiments, the inner layer includes cotton. In some embodiments, the inner layer has a thickness of at least one quarter inch. In some embodiments, the inner layer has a thickness of at most one inch.

In some embodiments, the outer layer of stretchable material is gathered in at least one area on the torso wrap. In some embodiments, the torso wrap is divided into a back panel attached between first and second front panels. In some embodiments, a first attachment panel is attached to the first front panel such that the first front panel is attached between the back panel and the first attachment panel, and the second attachment panel is attached to the second front panel such that the second front panel is attached between the back panel and the second attachment panel. In some embodiments, the first attachment panel attaches to the second attachment panel. In some embodiments, the first attachment panel attaches to the second attachment panel with a hook-and-loop fastening system. In some embodiments, the first front panel includes a first arc portion and the second front panel includes a second arc portion. In some embodiments, the first arc portion and the second arc portion form a continuous arc when the first attachment panel is attached to the second attachment panel. In some embodiments, the inner layer, middle layer, and outer layer are stitched together. In some embodiments, the stitching is elastic.

In another general aspect, the present invention provides a method of wearing a torso wrap to relieve back pain, the method including the steps of: providing a torso wrap having an inner layer of water-retaining material, a middle layer of moisture-barrier material, and an outer layer of stretchable material having first and second ends that secure to each other when the torso wrap is placed around the torso of a person; moistening the inner layer with water; placing the inner layer around a person's torso; and securing the first and second ends to each other to retain the torso wrap around the person's torso.

BRIEF DESCRIPTION OF THE DRAWINGS

Other features and advantages of the present invention will become apparent from reading the following detailed description, when considered in conjunction with the drawings.

FIG. 1 is a back view of the torso wrap of the present invention.

FIG. 2 is a top cross-sectional view of the three layers of the back panel portion of the torso wrap.

FIG. 3 is a back view of just the back panel portion of the of the torso wrap.

FIG. 4 is a front view of the torso wrap.

FIG. 5 is a back view of the torso wrap as worn on a human form seen from behind.

FIG. 6 is a front view of the torso wrap as worn on a human form seen from the front.

DETAILED DESCRIPTION

Directing attention to FIG. 1, there is shown generally a pain relief torso wrap 100. Torso wrap 100 includes a back panel 102 disposed between front panels 104A and 104B. Front panel 104A is disposed between back panel 102 and attachment panel 106A, and front panel 104B is disposed between back panel 102 and attachment panel 106B. Torso wrap 100 is worn by placing it around the lower portion of a person's torso, and attaching attachment panel 106A to attachment panel 106B. In a preferred embodiment, attachment panel 106A and 106B are a two-part hook-and-loop fastening system, such as found in hook-and loop fasteners similar to Velcro™ products. However, other fastening methods can also be utilized, such as buttons, zippers, buckles, cloth ties, and the like.

Directing attention to FIG. 2, back panel 102, and front panel 104A and 104B, utilize a three-layer system. In embodiments, an inner layer 202 is constructed from a stretchable, water-retaining, no-drip material such as white cotton, and preferably is 100% cotton. In other embodiments, middle moisture-barrier layer 204 is constructed from a medium-weight plastic material. In some embodiments, this plastic material of middle layer 204 is colorless or transparent. In other embodiments, the middle moisture barrier layer 204 is made of silicone, silicone rubber, or other rubber material. Middle layer 204 is gathered slightly within back panel 102 and gathered much more within front panels 104. Outer layer 206 is constructed from a drip-dry material that is stretchable to accommodate adjustment of torso wrap 100 while worn by a person. Layers 202, 204, and 206 are likewise stitched with an elastic thread to allow torso wrap 100 to stretch while being worn by a person.

Torso wrap 100 includes stitching of back panel 102, front panels 104A and 104B, and attachment panels 106A and 106B as a single unit, so inner layer 202 can remain wet while the outer layer 206 remains dry due to the moisture-barrier middle layer 204. In a preferred embodiment, inner layer 202 is only moistened with water and nothing else. Torso wrap 100 should be secured around the lower torso of a person so that it is snug, but not so tight that it is uncomfortable.

Directing attention to FIG. 3, back panel 102 is generally rectangular in shape, and in a preferred embodiment is approximately nine inches wide, but this dimension can be altered as needed based on the size of the person who wears torso wrap 100. Directing attention to FIG. 4, front panels 104A and 104B include a contoured lower edge 400 that forms an arc having a vertical dimension of approximately two inches, to accommodate the hip bone of the person wearing torso wrap 100.

As shown in FIG. 5, torso wrap 100 is worn by a person with the front panels 104A and 104B joined together across a person's belly, and attaches when attachment panels 106A and 106B are secured together through a hook-and-loop fastener system such as available through providers such as Velcro™ as described above, when attachment panels 106A and 106B are brought into contact with each other.

Directing attention to FIG. 6, torso wrap 100, when applied to the human form, places back panel 102 over the person's back, and when fastened as shown in FIG. 5. Because torso wrap 100 is fastened around the person's midsection in a secure manner, back panel 102 supports a person's lower back and places inner layer 202 directly against the skin of the user in the lower back.

Torso wrap 100 can be worn for approximately two hours to provide pain relief effects, but it can be worn for longer periods as well. Because inner layer 202 is made from a material such as cotton, and is typically used when moistened with water, it is important to keep inner layer 202 clean by occasionally washing inner layer 202 with a mild detergent and cold or warm water. Hot water is not recommended. Upon washing inner layer 202, it is recommended to pat it with a clean sponge to absorb as much water as possible. It is important not to use harsh products such as bleach when washing inner layer 202 so as not to irritate the skin of the person wearing torso wrap 100.

Similarly, outer layer 206 is best cleaned with mild detergent and cold or warm water and allowed to drip dry. As dyes can also irritate skin, inner layer 202 and middle layer 204 are colorless to avoid placing dyes in contact with the skin of the person wearing torso wrap 100. As inner layer 202 is wet, it is recommended that the person wearing torso wrap 100 not handle any electrical equipment or devices. It is also recommended that the wearer be soap-and-water clean before wearing torso wrap 100, as there should be no residues of any kind of the wearer's skin before applying torso wrap 100.

To use torso wrap 100, open torso wrap 100 and lay its full length flat. Using a new kitchen sponge sold with torso wrap 100 (so that the sponge remains clean and only used with torso wrap 100 so that it remains free of contaminants), wash torso wrap 100 before using it. Dip torso wrap 100 in a container of tepid water so that inner layer 202 becomes evenly saturated. Gently squeeze out excess water from inner layer 202 until it no longer drips. If still too wet, use the provided sponge to remove excess water until the desired amount of moistness is achieved. Place torso wrap 100 around the lower torso, with back panel 102 over the wearer's lower back, and join fastening panels 106A and 106B together over the wearer's belly. Torso wrap 100 can be worn while standing, sitting, lying down, or while moving. It can be worn indoors only.

In the preferred embodiment of the invention, the inner layer is fabricated of white cotton, no drip material.

While a torso wrap having three layers has been described and illustrated in detail herein, it is to be understood that numerous changes and variations can be made to various embodiments of the present invention without departing from the spirit and scope of the following claims.

What is claimed is:

1. A method of providing a torso wrap on a wearer with a torso, the method adapted to relieve pain, the method comprising:
providing the torso wrap having a first front panel and a second front panel, the torso wrap having a back panel between and attached to the first front panel and second front panel, a first attachment panel attached to the first front panel such that the first front panel is attached between the back panel and the first attachment panel, a second attachment panel attached to the second front panel such that the second front panel is attached between the back panel and the second attachment panel, the first attachment panel being attached to the second attachment panel with hook and loop fasteners, the first front panel including a first arc portion and the second front panel including a second arc portion, the first arc portion and the second arc portion forming a continuous arc when the first attachment panel is attached to the second attachment panel; wherein the first front panel, the second front panel and the back panel each comprise an inner layer, a middle layer, and an outer layer the inner layer comprising a water retaining cotton material to be worn in direct contact with the torso, the inner layer having a thickness, the middle layer comprising a moisture barrier material in contact with the inner layer, and the outer layer comprising a stretchable material in contact with the middle layer, the outer layer being gathered in at least one area of the torso wrap, elastic stitching coupling the inner layer, the middle layer, and the outer layer;
moistening the inner layer with water prior to wearing;
placing the inner layer in direct contact with and around the wearer's torso; and
securing the first attachment panel and the second attachment panel to each other to retain the torso wrap around the torso.

* * * * *